United States Patent [19]
Gerster et al.

[11] Patent Number: 6,150,523
[45] Date of Patent: Nov. 21, 2000

[54] PROCESS FOR PREPARING IMIDAZOQUINOLINAMINES

[75] Inventors: John F. Gerster, Woodbury, Minn.; Kyle J. Lindstrom, Houlton, Wis.

[73] Assignee: 3M Innovative Properties Company, St. Paul, Minn.

[21] Appl. No.: 09/375,587

[22] Filed: Aug. 17, 1999

Related U.S. Application Data

[62] Division of application No. 09/061,401, Apr. 16, 1998, Pat. No. 5,998,619, which is a continuation of application No. 08/673,712, Jun. 21, 1996, Pat. No. 5,741,908.

[51] Int. Cl.$^7$ ............................ C07F 9/58; C07D 471/04; C07D 471/12
[52] U.S. Cl. ............................ 546/23; 546/82; 514/293
[58] Field of Search ..................................... 546/82, 23

[56] References Cited

U.S. PATENT DOCUMENTS

| | | | |
|---|---|---|---|
| 3,764,681 | 10/1973 | Dreikorn | 514/293 |
| 3,891,653 | 6/1975 | Dreikorn | 546/82 |
| 4,689,338 | 8/1987 | Gerster | 514/293 |
| 4,698,348 | 10/1987 | Gerster | 514/293 |
| 4,929,624 | 5/1990 | Gerster et al. | 514/293 |
| 4,988,815 | 1/1991 | Andre et al. | 546/159 |
| 5,175,296 | 12/1992 | Gerster | 546/82 |
| 5,266,575 | 11/1993 | Gerster et al. | 514/293 |
| 5,268,376 | 12/1993 | Gerster | 514/293 |
| 5,346,905 | 9/1994 | Gerster | 514/293 |
| 5,367,076 | 11/1994 | Gerster | 546/82 |
| 5,389,640 | 2/1995 | Gerster et al. | 514/293 |
| 5,395,937 | 3/1995 | Nikolaides et al. | 546/82 |
| 5,525,612 | 6/1996 | Gerster | 514/293 |
| 5,578,727 | 11/1996 | Andre et al. | 546/82 |
| 5,602,256 | 2/1997 | Andre et al. | 546/180 |
| 5,605,899 | 2/1997 | Gerster et al. | 546/82 |
| 5,693,811 | 12/1997 | Lindstrom | 546/82 |
| 5,714,608 | 2/1998 | Gerster | 546/82 |
| 5,741,908 | 4/1998 | Gerster et al. | 514/293 |
| 5,756,747 | 5/1998 | Gerster | 514/293 |

FOREIGN PATENT DOCUMENTS

| | | |
|---|---|---|
| 0 385 630 | 2/1990 | European Pat. Off. . |
| 94/17043 | 8/1994 | WIPO . |

OTHER PUBLICATIONS

Chemistry of Heterocyclic Compounds (Englis Edition) 1981, 16, (12), 1286–1288 (Zyryanov).
J. Prakt. Chem., 336 (1994), 311–318 (Steinschifter).

*Primary Examiner*—Alan L. Rotman
*Attorney, Agent, or Firm*—MarySusan Howard; Ted K. Ringsred; Robert W. Sprague

[57] ABSTRACT

A process for preparing 1H-imidazo[4,5-c]quinolin-4-amines is disclosed. The process involves reacting a 6H-imidazo[4,5-c]tetrazolo[1,5-a]quinoline with triphenylphosphine and hydrolyzing the product thereof.

6 Claims, No Drawings

PROCESS FOR PREPARING IMIDAZOQUINOLINAMINES

This is a divisional of application Ser. No. 09/061,401 filed Apr. 16, 1998, now U.S. Pat. No. 5,998,619, which is a continuation of application Ser. No. 08/673,712, filed Jun. 21, 1996, now U.S. Pat. No. 5,741,908.

BACKGROUND OF THE INVENTION

1. Technical Field

This invention relates to processes for preparing 1H-imidazo[4,5-c]quinolin-4-amines and to intermediates for use in preparing 1H-imidazo[4,5-c]quinolin-4-amines.

2. Description of the Related Art

Certain antiviral immunomodulator 1H-imidazo[4,5-c]quinolin-4-amines and methods for their preparation are known and disclosed. For example U.S. Pat. Nos. 4,689,338 and 4,929,624 (Gerster) disclose a method involving the step of heating the corresponding 4-chloro compound in the presence of ammonium hydroxide or ammonia under pressure to provide the 4-amino compound. U.S. Pat. No. 4,988,815 (Andre) discloses a process involving amination of the 4-position of a 3-nitro-1,4-dichloroquinoline. This process too involves as a final step the reaction of ammonia with a 4-chloro-1H-imidazo[4,5-c]quinoline.

Milder methods have been used in order to introduce the 4-amino group of 1H-imidazo[4,5-c]quinolin-4-amines. U.S. Pat. No. 5,175,296 (Gerster) discloses a process involving the reaction of a 1H-imidazo[4,5-c]quinoline 5N-oxide with an organic isocyanate and hydrolyzing the product to provide the 4-amino compound. U.S. Pat. No. 5,367,076 (Gerster) discloses a process involving the reaction of a 1H-imidazo[4,5-c]quinoline 5N-oxide with an acylating agent and reacting the product with an aminating agent to provide the 4-amino compound. U.S. Pat. No. 5,395,937 (Nikolaides) discloses a process involving amination of the 4-position of a 3-nitroquinoline-2,4-disulfonate with a substituted amine. The final step of the process involves hydrogenolysis to provide the 4-amino compound.

SUMMARY OF THE INVENTION

This invention provides a process for preparing a 1H-imidazo[4,5-c]quinolin-4-amine comprising the steps of:

(i) providing a tetrazolo[1,5-a]quinolin-5-ol;

(ii) nitrating the compound from step (i) to provide a 4-nitrotetrazolo[1,5-a]quinolin-5-ol;

(iii) sulfonylating the compound from step (ii) to provide a 4-nitrotetrazolo[1,5-a]quinolin-5-sulfonate;

(iv) reacting the compound from step (iii) with an amine to provide a (5-substituted)-4-nitrotetrazolo[1,5-a]quinolin-5-amine;

(v) reducing the compound from step (iv) to provide a (5-substituted)tetrazolo[1,5-a]quinolin-4,5-diamine;

(vi) reacting the compound from step (v) with a carboxylic acid or an equivalent thereof to provide a (5-substituted) (6-substituted) 6H-imidazo[4,5-c]tetrazolo[1,5-a]quinoline;

(vii) reacting the compound from step (vi) with triphenylphosphine to provide a (1-substituted) (2-substituted) N-triphenylphosphinyl-1H-imidazo[4,5-c]quinolin-4-amine;

(viii) hydrolyzing the compound from step (vii) to provide a (1-substituted) (2-substituted) 1H-imidazo[4,5-c]quinolin-4-amine; and (xi) isolating the (1-substituted) (2-substituted) 1H-imidazo[4,5-c]quinolin-4-amine or a pharmaceutically acceptable addition salt thereof.

This invention also provides a process for preparing a 1H-imidazo[4,5-c]quinolin-4-amine comprising the steps of:

(i) providing a (4-substituted) amino-2-chloro-3-nitroquinoline;

(ii) reacting the compound from step (i) with sodium azide to provide (5-substituted)-4-nitrotetrazolo[1,5-a]quinolin-5-amine;

(iii) reducing the compound from step (ii) to provide a (5-substituted)tetrazolo[1,5-a]quinolin-4,5-diamine;

(iv) reacting the compound from step (iii) with a carboxylic acid or an equivalent thereof to provide a (5-substituted) (6-substituted) 6H-imidazo[4,5-c]tetrazolo[1,5-a]quinoline;

(v) reacting the compound from step (iv) with triphenylphosphine to provide a (1-substituted) (2-substituted) N-triphenylphosphinyl-1H-imidazo[4,5-c]quinolin-4-amine;

(vi) hydrolyzing the compound from step (v) to provide a (1-substituted) (2-substituted) 1H-imidazo[4,5-c]quinolin-4-amine; and (vii) isolating the (1-substituted) (2-substituted) 1H-imidazo[4,5-c]quinolin-4-amine or a pharmaceutically acceptable addition salt thereof.

This invention also provides a process for preparing a 1H-imidazo[4,5-c]quinolin-4-amine comprising the steps of:

(i) providing a (1-substituted) (2-substituted) 4-chloro-1H-imidazo[4,5-c]quinoline;

(ii) reacting the compound from step (i) with hydrazine to provide a (1-substituted) (2-substituted) 4-hydrazino-1H-imidazo[4,5-c]quinoline;

(iii) reacting the compound from step (ii) with sodium nitrite to provide a (5-substituted) (6-substituted) 6H-imidazo[4,5-c]tetrazolo[1,5-a]quinoline;

(iv) reacting the compound from step (iii) with triphenylphosphine to provide a (1-substituted) (2-substituted) N-triphenylphosphinyl-1H-imidazo[4,5-c]quinolin-4-amine;

(v) hydrolyzing the compound from step (iv) to provide a (1-substituted) (2-substituted) 1H-imidazo[4,5-c]quinolin-4-amine; and (vi) isolating the (1-substituted) (2-substituted) 1H-imidazo[4,5-c]quinolin-4-amine or a pharmaceutically acceptable addition salt thereof.

This invention also provides processes involving certain of the various individual steps set forth above, and combinations of such steps.

In another aspect this invention also provides 4-nitrotetrazolo[1,5-a]quinolin-5-ols, 4-nitrotetrazolo[1,5-a]quinoline-5-sulfonates, (5-substituted)-4-nitrotetrazolo[1,5-a]quinolin-5-amines, (5-substituted)tetrazolo[1,5-a]quinolin-4,5-diamines, (5-substituted) (6-substituted) 6H-imidazo[4,5-c]tetrazolo[1,5-a]quinolines, (1-substituted) (2-substituted) 4-hydrazino-1H-imidazo[4,5-c]quinolines, and (1-substituted) (2-substituted) N-triphenylphosphinyl-1H-imidazo[4,5-c]quinolin-4-amines.

DETAILED DESCRIPTION OF THE INVENTION

Substituents designated parenthetically herein indicate that the substituent is optionally present, e.g., a 4-(substituted) amino compound contains either an unsubstituted 4-amino group or a substituted 4-amino group.

Reaction Scheme I illustrates processes of the invention and the preparation of compounds of the invention. The unsubstituted compound of Formula I is a known compound and other compounds of Formula I can be prepared by methods known to those skilled in the art and disclosed, e.g., in *Chemistry of Heterocyclic Compounds* (English Edition), 1981, 16, (12), 1286–1288 (Zyryanov).

displaced. A particularly preferred sulfonic anhydride is trifluoromethanesulfonic anhydride.

The reaction is preferably carried out by combining a compound of Formula II with a base, preferably an excess of a tertiary amine base (e.g., a trialkylamine base such as triethyl amine) in a suitable solvent such as dichloromethane and then adding the sulfonyl halide or sulfonic anhydride. The addition is preferably carried out in a controlled fashion (e.g., dropwise) and at a reduced temperature (e.g., about 0°

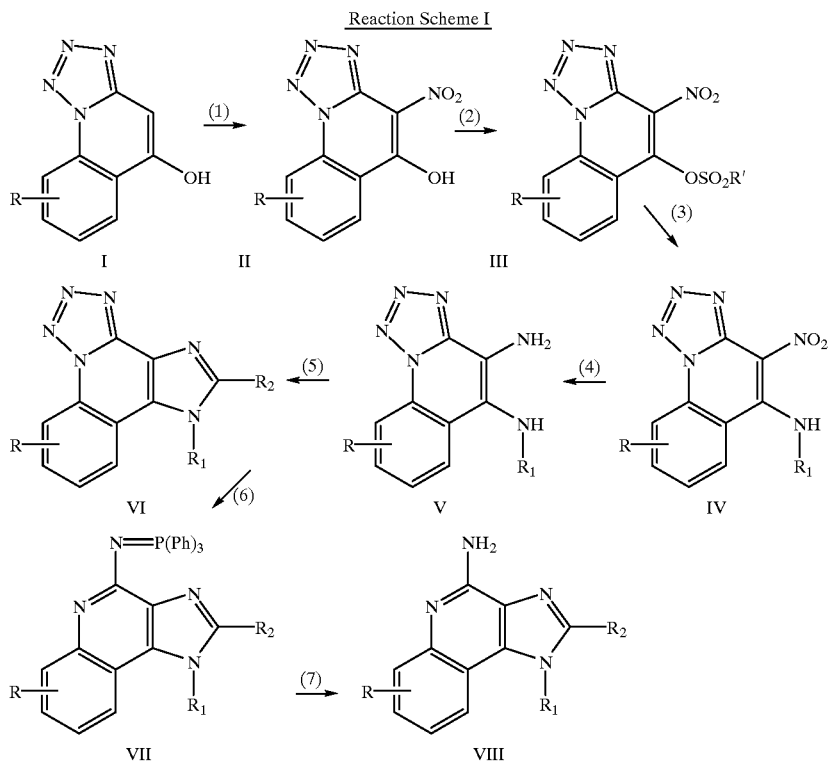

Reaction Scheme I

In step (1) of Reaction Scheme I a 4-nitrotetrazolo[1,5-a]quinolin-5-ol of Formula II is provided by nitrating a tetrazolo[1,5-a]quinolin-5-ol of Formula I. Conventional conditions for such reactions are well known. Preferred conditions in the instance where R is hydrogen involve heating in acetic acid in the presence of nitric acid. Preferred conditions in other instances will depend upon the particular tetrazolo[1,5-a]quinolin-5-ol used, and those skilled in the art will be able to select suitable conditions. The product can be isolated from the reaction mixture using conventional methods.

In step (2) of Reaction Scheme I a 4-nitrotetraozolo[1,5-a]quinolin-5-sulfonate of Formula III is provided by reacting a 4-nitrotetrazolo[1,5-a]quinolin-5ol of Formula II with a sulfonyl halide or preferably a sulfonic anhydride. Suitable sulfonyl halides include alkylsulfonyl halides such as methanesulfonyl chloride and trifluoromethanesulfonyl chloride, and arylsulfonyl halides such as benzenesulfonyl chloride, p-bromobenzenesulfonyl chloride and p-toluenesulfonyl chloride. Suitable sulfonic anhydrides include those corresponding to the above-mentioned sulfonyl halides. Sulfonic anhydrides are preferred in view of the fact that the sulfonate anion generated as a by-product of the reaction is a relatively poor nucleophile and as such does not give rise to undesired side products such as those in which the nitro group is C.). The product can be isolated by conventional methods or it can be carried on without isolation as described below in connection with step (3).

In step (3) of Reaction Scheme I a (5-substituted) 4-nitrotetrazolo[1,5-a]quinolin-5-amine of Formula IV is provided by reacting a 4-nitrotetrazolo[1,5-a]quinolin-5-sulfonate of Formula III with an amine, preferably in the presence of an excess of an amine base in a solvent such as dichloromethane. Suitable amines include ammonia and preferably primary amines. Primary amines provide 5-substituted amino compounds of Formula IV wherein the amino substituent is represented by $R_1$. Particularly preferred amines include isobutylamine and 2-aminomethyl-2-propanol.

The reaction can be carried out by adding an excess of amine to the reaction mixture resulting from Step (2). The reaction can also be carried out by adding an excess of amine to a solution of the compound of Formula III in a solvent such as dichloromethane. As the sulfonate is a relatively facile leaving group the reaction can be run at ambient temperature. The product can be isolated from the reaction mixture using conventional methods.

In step (4) of Reaction Scheme I a (5-substituted)tetrazolo[1,5-a]quinolin-4,5-diamine of Formula V is provided by reducing a (5-substituted) 4-nitrotetrazolo[1,5-a]quinolin-5- amine of Formula IV. Methods for such reduction are well know to those skilled in the art. Preferably the reduction is carried out using a conventional heterogeneous hydrogenation catalyst such as platinum on carbon or palladium on carbon. The reduction can be conveniently carried out on a Paar apparatus in a solvent such as ethanol. The product can be isolated from the reaction mixture using conventional methods.

In step (5) of Reaction Scheme I a (5-substituted) (6-substituted) 6H-imidazo[4,5-c]tetrazolo[1,5-a]quinoline of Formula VI is provided by reacting a (5-substituted) tetrazolo[1,5-a]quinolin-4,5-diamine of Formula V with a carboxylic acid or an equivalent thereof. Suitable equivalents to carboxylic acid include acid halides, orthoesters, and 1,1-dialkoxyalkyl alkanoates. The carboxylic acid or equivalent is selected such that it will give rise to the desired 6-substituent in the compound of Formula VI wherein the 6-substituent is designated $R_2$ (e.g., acetyl chloride will give rise to a compound where $R_2$ is methyl). The reaction can be run in the absence of solvent or preferably in an inert solvent in the presence of a carboxylic acid or equivalent thereof with sufficient heating to drive off any alcohol or water formed as a side product of the reaction. The product can be isolated from the reaction mixture using conventional methods.

In step (6) of Reaction Scheme I a (1-substituted) (2-substituted) N-triphenylphosphinyl-1H-imidazo[4,5-c] quinolin-4-amine of Formula VII is provided by reacting a (5-substituted) (6-substituted) 6H-imidazo[4,5-c]tetrazolo [1,5]quinoline of Formula VI with triphenylphosphine. The reaction can be carried out by combining a compound of Formula VI with triphenylphosphine in a suitable solvent such as 1,2-dichlorobenzene and heating. The product can be isolated from the reaction mixture using conventional methods.

In step (7) of Reaction Scheme I a (1-substituted) (2-substituted) 1H-imidazo[4,5-c]quinoline-4-amine of Formula VIII is provided by hydrolysis of a (1-substituted) (2-substituted) N-triphenylphosphinyl-1H-imidazo[4,5-c] quinolin-4-amine of Formula VII. Such a reaction can be carried out by general methods well known to those skilled in the art (e.g., by heating in a lower alkanol in the presence of an acid). The product can be isolated from the reaction mixture by conventional means.

In Reaction Scheme I, R' can be any group that can be incorporated into a sulfonyl halide or a sulfonic anhydride. Alkyl (e.g., methyl), haloalkyl including perfluoroalkyl (e.g., trifluoromethyl) and aryl (e.g., phenyl, halophenyl and tolyl) are all suitable.

Reaction Scheme II illustrates processes of the invention and the preparation of compounds of the invention. Compounds of Formula IX and methods for their preparation are known and disclosed, e.g. in U.S. Pat. Nos. 4,988,815 (Andre), and 5,268,376 (Gerster), both patents being incorporated herein by reference.

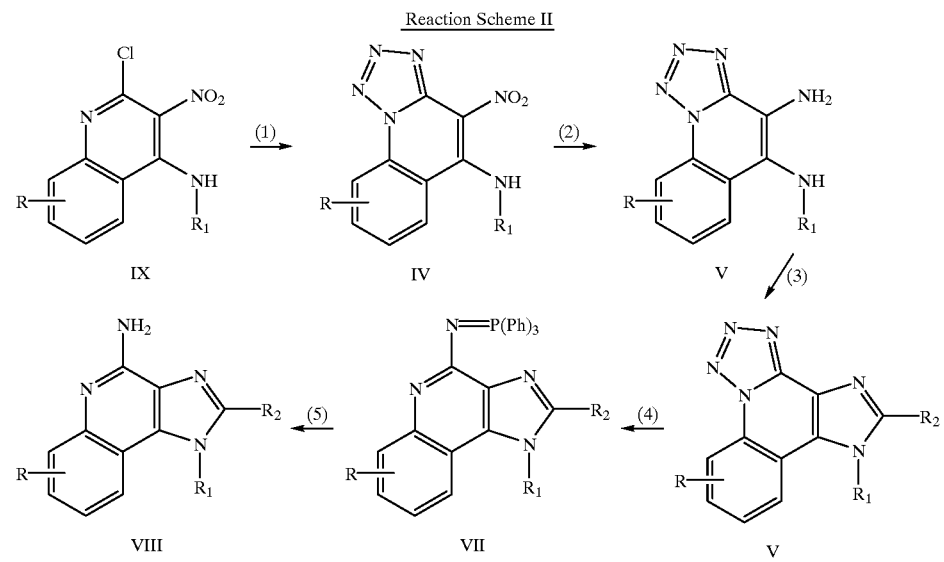

Reaction Scheme II

In step (1) of Reaction Scheme II a (5-substituted) 4-nitrotetrazolo[1,5-a]quinolin-5-amine of Formula IV is provided by reacting a (4-substituted) amino-2-chloro-3-nitroquinoline of Formula IX with sodium azide. The reaction can be carried out by combining the compound of Formula IX with sodium azide in a suitable solvent such as N,N-dimethylformamide and heating (about 50° C.). The product can be isolated from the reaction mixture using conventional methods.

Steps (2), (3), (4) and (5) of Reaction Scheme II can be carried out in the same manner as steps (4), (5), (6) and (7) of Reaction Scheme I respectively.

Reaction Scheme III illustrates processes of the invention and the preparation of compounds of the invention. Compounds of Formula X and methods for their preparation are known and disclosed, e.g., in European Patent Application 90.301776.3, U.S. Pat. Nos. 4,689,338 (Gerster), 4,698,348 (Gerster), 4,929,625 (Gerster), 4,988,815 (Andre), 5,268, 376 (Gerster), and 5,389,640 (Gerster) all six patents being incorporated herein by reference.

Reaction Scheme III

In step (1) of Reaction Scheme III a (1-substituted)(2-substituted) 4-hydrazino-1H-imidazo[4,5-c]quinoline of Formula XI is provided by reacting a (1-substituted)(2-substituted) 4-chloro-1H-imidazo[4,5-c]quinoline of Formula X with hydrazine. The reaction can be carried out by combining a compound of Formula X with an excess of hydrazine and heating if necessary. The product can be isolated from the reaction mixture using conventional methods.

In step (2) of Reaction Scheme III a (5-substituted)(6-substituted) 6H-imidazo[4,5-c]tetrazolo[1,5-a]quinoline of Formula VI is provided by reacting a (1-substituted)(2-substituted) 4-hydrazino-1H-imidazo[4,5-c]quinoline of Formula XI with sodium nitrite. The reaction can be carried out by combining the compound of Formula XI with sodium nitrite in a suitable solvent (e.g., water) in the presence of an acid (e.g., acetic acid). The product can be isolated from the reaction mixture using conventional methods.

Steps (3) and (4) of Reaction Scheme III can be carried out in the same manner as steps (6) and (7) of Reaction Scheme I respectively.

The compounds of Formula VIII can be used in the form of acid addition salts such as hydrochlorides, dihydrogen sulfates, trihydrogen phosphates, hydrogen nitrates, methane sulfonates and salts of other pharmaceutically acceptable acids. Pharmaceutically acceptable acid addition salts of Formula VIII are generally prepared by reaction of the respective compound with an equimolar amount of a strong acid, preferably an inorganic acid such as hydrochloric, sulfuric or phosphoric acid or an organic acid such as methanesulfonic acid in a polar solvent. Isolation of the salt is facilitated by the addition of a solvent in which the salt is insoluble (e.g., diethyl ether).

Processes of the invention provide as a final product a 1H-imidazo[4,5-c]quinolin-4-amine, preferred embodiments of which can be represented by Formula VIII.

Preferably the 1H-imidazo[4,5-c]quinolin-4-amine is a compound defined by one of Formulas XXI–XXV below:

XXI wherein $R_{11}$ is selected from the group consisting of alkyl, hydroxyalkyl, acyloxyalkyl, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that if said benzene ring is substituted by two of said moieties, then said moieties together contain no more than 6 carbon atoms; acylaminoalkyl wherein the alkyl moiety contains two to four carbon atoms; disubstituted aminoalkyl wherein the alkyl moiety contains two to four carbon atoms; morpholinoalkyl wherein the alkyl moiety contains two to four carbon atoms; $R_{21}$ is selected from the group consisting of hydrogen, alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that when the benzene ring is substituted by two of said moieties, then the moieties together contain no more than 6 carbon atoms; and each $R_A$ is independently selected from the group consisting of alkoxy of one to about four carbon atoms, halogen and alkyl of one to about four carbon atoms, and n is an integer from 0 to 2, with the proviso that if n is 2, then said $R_A$ groups together contain no more than 6 carbon atoms;

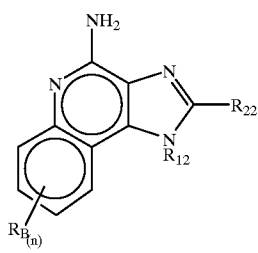

XXII wherein $R_{12}$ is selected from the group consisting of straight chain or branched chain alkenyl containing 2 to about 10 carbon atoms and substituted straight chain or branched chain alkenyl containing 2 to about 10 carbon atoms, wherein the substituent is selected from the group consisting of straight chain or branched chain alkyl containing 1 to about 4 carbon atoms and cycloalkyl containing 3 to about 6 carbon atoms; and cycloalkyl containing 3 to about 6 carbon atoms substituted by straight chain or branched chain alkyl containing 1 to about 4 carbon atoms; and $R_{22}$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than 6 carbon atoms; and each $R_B$ is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said $R_B$ groups together contain no more than 6 carbon atoms;

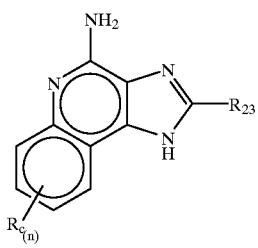

XXIII wherein $R_{23}$ is selected from the group consisting of hydrogen, straight chain or branched chain alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to about four carbon atoms, straight chain or branched chain alkoxy of one to about four carbon atoms, and halogen, with the proviso that when the benzene ring is substituted by two such moieties, then the moieties together contain no more than 6 carbon atoms; and each $R_C$ is independently selected from the group consisting of straight chain or branched chain alkoxy of one to about four carbon atoms, halogen, and straight chain or branched chain alkyl of one to about four carbon atoms, and n is an integer from zero to 2, with the proviso that if n is 2, then said $R_C$ groups together contain no more than 6 carbon atoms;

XXIV wherein $R_{14}$ is —$CHR_xR_y$
wherein $R_y$ is hydrogen or a carbon-carbon bond, with the proviso that when $R_y$ is hydrogen $R_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from the group consisting of hydroxy and hydroxyalkyl of one to about four carbon atoms;

$R_{24}$ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and $R_D$ is selected from the group consisting of hydrogen, straight chain or branched chain alkoxy containing one to about four carbon atoms, halogen, and straight chain or branched chain alkyl containing one to about four carbon atoms;

XXV wherein $R_{15}$ is selected from the group consisting of: hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms; acylaminoalkyl wherein the alkyl moiety contains two to four carbon atoms; disubstituted aminoalkyl wherein the alkyl moiety contains two to four carbon atoms; morpholinoalkyl wherein the alkyl moiety contains two to four carbon atoms;

$R_{25}$ is

wherein $R_S$ and $R_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms; and $R_E$ is selected from the group consisting of hydrogen, straight chain or branched chain alkoxy containing one to about four carbon atoms, halogen, and straight chain or branched chain alkyl containing one to about four carbon atoms;

or a pharmaceutically acceptable salt of any of the foregoing.

The compounds recited above are disclosed and claimed in the several patents noted above in the Summary of the Invention and discussed below.

In instances where n can be zero, one, or two, n is preferably zero or one.

The substituents $R_A$–$R_E$ above are species embraced by R. The preferred R substituent is hydrogen.

The substituents $R_{11}$–$R_{15}$ above are species embraced by $R_1$. The preferred $R_1$ substituents are alkyl of one to about six carbon atoms, hydroxy alkyl wherein the alkyl moiety contains one to about 6 carbon atoms, and arylalkyl wherein the alkyl moiety contains one to about three carbon atoms. Most preferably the $R_1$ substituent is 2-methylpropyl, 2-hydroxy-2-methylpropyl, benzyl or phenylethyl.

The substituents $R_{21}$–$R_{25}$ above are species embraced by $R_2$. The preferred $R_2$ substituents are hydrogen, alkyl of one to about four carbon atoms, alkoxyalkyl wherein the alkoxy moiety contains one to about four carbon atoms and the alkyl moiety contains one to about four carbon atoms, hydroxyl alkyl wherein the alkyl moiety contains one to about four carbon atoms, haloalkyl wherein the alkyl moiety contains one to about four carbon atoms, and aryloxymethyl. Most preferably the $R_2$ substituent is hydrogen, methyl, ethoxymethyl, or benzyl.

Certain R substituents, $R_1$ substituents, and $R_2$ substituents will be incompatible with the particular reaction conditions described above in connection with the Reaction Schemes. Those skilled in the art, however, will be able to select alternative conditions under which the several steps can be carried out and/or methods of functional group protection and manipulation that will allow the use of the processes of the invention in the preparation of 1H-imidazo[4,5-c]quinolin-4-amines of diverse structures.

Certain 1H-imidazo[4,5-c]quinolin-4-amines have been disclosed as antiviral agents (see, e.g., European Patent Application 90.301776.3 (Gerster), U.S. Pat. Nos. 4,689,338 (Gerster), 4,929,624 (Gerster), 5,266,575 (Gerster), 5,268,376 (Gerster), and 5,389,640 (Gerster) all five patents incorporated herein by reference). Certain of these compounds are also known to induce biosynthesis of cytokines such as interferons, interleukins, and tumor necrosis factor in humans and in mice.

The Examples below are intended to illustrate the invention. All parts and percentages are by weight unless otherwise indicated.

EXAMPLE 1

Tetrazolo[1,5-a]quinolin-5-ol

Part A

Anthranilic acid (274.3 g) and acetic anhydride (1.1 L) were combined then heated at reflux for 3.5 hours. The reaction mixture was concentrated under vacuum. The residue was combined with methanol (550 mL) then concentrated under vacuum to provide 2-methyl-4-oxo-3,1-benzoxazine as a brown oil.

Part B

The crude 2-methyl-4-oxo-3,1-benzoxazine was dissolved in acetic acid (1.9 L). Sodium azide (130.0 g) was added to the solution in portions with stirring. The reaction mixture was cooled in an ice bath to maintain the reaction temperature at 25 to 30° C. during the addition. The reaction mixture was allowed to stir at ambient temperature over the weekend. The acetic acid was removed under vacuum to provide a white solid. The solid was combined with 10% sodium hydroxide (1.4 L) then heated on a steam bath for 1 hour. Additional sodium hydroxide (120 g of 50% sodium hydroxide) was added. The mixture was heated on a steam bath for an additional hour then allowed to cool to ambient temperature overnight. Additional sodium hydroxide (120 g of 50% sodium hydroxide) was added. The mixture was heated on a steam bath for 2 hours then allowed to cool. The reaction mixture was poured with rapid stirring into a mixture of concentrated hydrochloric acid (1.0 L) and ice (3 L). The resulting mixture was stirred at ambient temperature overnight. A precipitate was isolated by filtration, rinsed with water then slurried with water (4 L). The solid was isolated by filtration, rinsed with water then oven dried at 50° C. to provide 278.0 g of crude 2-(5-methyl-1H-tetrazol-1-yl)benzoic acid as a tan solid, m.p. 157–160° C. The crude material was dissolved in 10% sodium hydroxide (2.5 L). The resulting solution was heated (95–99° C.) for 2.5 hours, cooled, then poured with vigorous stirring into a mixture of concentrated hydrochloric acid (500 mL) and ice (5 L). The resulting mixture was allowed to stir for 2 hours. The precipitate was isolated by filtration, rinsed with water, then slurried with water (3 L). The solid was isolated by filtration, rinsed with water then dried overnight at ambient temperature to provide 228 g of 2-(5-methyl-1H-tetrazol-1-yl)benzoic acid, m.p. 164–166° C.

Part C

Acetone (3.2 L) and 2-(5-methyl-1H-tetrazol-1-yl)benzoic acid (228 g) were combined then stirred at ambient temperature for 15 minutes. Potassium carbonate (228 g) was added to the reaction mixture in a single portion. Iodoethane (366.8 g) was added dropwise to the reaction mixture producing a slight exotherm. The reaction mixture was heated at reflux for about 4 hours then stirred overnight while cooling to ambient temperature. The precipitated salts were removed by filtration then rinsed with acetone. The combined filtrates were evaporated under vacuum. The residue was dissolved in dichloromethane (1.5 L). The dichloromethane solution was washed with water (1.5 L), dried over magnesium sulfate then concentrated under vacuum to provide 227 g of ethyl-2-(5-methyl-1H-tetrazol-1-yl)benzoate as a white solid m.p. 98–100° C.

Part D

Potassium ethoxide (173.5 g) was added in portions with stirring to a mixture of ethyl-2-(5-methyl-1H-tetrazol-1-yl)benzoate (227 g) and N,N-dimethylformamide (1.6 L). The reaction mixture was cooled with an ice bath to control the resulting exotherm. The reaction mixture was stirred overnight at ambient temperature then quenched with water (17 L). The pH was adjusted to pH 5 with acetic acid (170 mL). The resulting precipitate was isolated by filtration, rinsed with water then reslurried with water (2.5 L). The solid was isolated by filtration, rinsed with water then oven dried (55 to 60° C.) for 16 hours to provide 169.0 g of a white solid. A 3.0 g sample was recrystallized from ethanol/dichloromethane to provide tetrazolo[1,5-a]quinolin-5-ol as a white solid, m.p. 248° C. (dec.). Analysis: Calculated for $C_9H_6N_4O$: %C, 58.06; %H, 3.25; %N, 30.09; Found: %C, 58.02; %H, 3.29; %N, 30.20.

EXAMPLE 2

4-Nitrotetrazolo[1,5-a]quinolin-5-ol Hydrate

Tetrazolo[1,5-a]quinolin-5-ol (10 g, 54 mmole, Example 1) was suspended in acetic acid (200 mL) then warmed to 40° C. Nitric acid (4 mL of 16M, 59 mmole) was added to the reaction mixture. The reaction mixture was heated at 80° C. for 30 minutes then allowed to cool to ambient temperature. The resulting precipitate was isolated by filtration, rinsed with water then recrystallized from isopropanol/water to provide 8.1 g of 4-nitrotetrazolo[1,5-a]quinolin-5-ol hydrate as light yellow plates, m.p. 186.5–187° C. Analysis: Calculated for $C_9H_5N_5O_3 \cdot H_2O$: %C, 43.38; %H, 2.83; %N, 28.10; Found: %C, 43.27; %H, 2.84; %N, 28.25.

EXAMPLE 3

2-Methyl-[(4-nitro-5-tetrazolo[1,5-a]quinolinyl)amino]-2-propanol

Sodium azide (19.5 g, 0.3 moles), 2-methyl-[(2-chloro-3-nitroquinolin-4-yl)amino]-2-propanol (29.6 g, 0.10 mole, U.S. Pat. No. 4,988,815 Example 12) and N,N-dimethylformamide (100 mL) were added to a jacketed 1 liter round bottom flask with the outside portion containing acetone. The reaction mixture was stirred with a stirring bar and the acetone refluxed to provide a constant internal reaction temperature of 53° C. After 18 hours the reaction mixture was diluted with water (100 mL). The resulting yellow precipitate was isolated by filtration then washed with 50% N,N-dimethylformamide/water until the washes became light colored. The yellow/green solid was then washed with water, pressed dry and washed with ether. The solid was air dried to provide 27.2 g of crude product as a yellow/light green solid. This material was recrystallized from ethanol/dichloromethane to provide 2-methyl-[(4-nitro-5-tetrazolo[1,5-a]quinolinyl)amino]-2-propanol as a yellow crystalline solid, m.p. 204° C. (dec.). Analysis: Calculated for: $C_{13}H_{14}N_6O_3$: %C, 51.65; %H, 4.67; %N, 27.8; Found: %C, 51.30; %H, 4.69; %N, 27.43.

EXAMPLE 4

[(4-Amino-5-tetrazolo[1,5-c]quinolinyl)amino]-2-methyl-2-propanol

2-Methyl-[(4-nitro-5-tetrazolo[1,5a]quinolinyl)amino]-2-propanol (30.2 g, 0.10 mole, Example 3), ethanol (300 mL) and 5% Pd/C (1.0 g of 50% water wet) were placed in a Paar apparatus. The mixture was hydrogenated. The mixture was diluted with dichloromethane then filtered to remove the catalyst. The filtrate was concentrated under vacuum. The crude product was recrystallized from ethanol to provide 20.5 g of [(4-amino-5-tetrazolo[1,5-c]quinolinyl)amino]-2-methyl-2-propanol as a yellow/green crystalline solid, m.p. 164–167° C. Analysis: Calculated for $C_{13}H_{16}N_6O$: %C, 57.33; %H, 5.92; %N, 30.88; Found: %C, 56.94; %H, 5.88; %N, 30.80.

EXAMPLE 5

α,α-Dimethyl-6H-imidazo[4,5-c]tetrazolo[1,5-a]quinoline-6-ethanol

[(4-Amino-5-tetrazolo[1,5-c]quinolinyl)amino]-2-methyl-2-propanol (5 g, 0.18 mole, Example 4) was dissolved in triethyl orthoformate (17 g). The solution was heated at 120° C. for 20 hours. The reaction mixture was allowed to cool to ambient temperature then it was diluted with 1 N hydrochloric acid. Formic acid (20 mL) was added to the mixture which was then heated at reflux for an hour. The reaction mixture was concentrated under vacuum then neutralized with sodium hydroxide. The crude product was recrystallized from ethanol/ethyl acetate to provide α,α-dimethyl-6H-imidazo[4,5-c]tetrazolo[1,5-a]quinoline-6-ethanol as a solid, m.p. 245–248° C. Analysis: Calculated for $C_{14}H_{14}N_6O$: %C, 59.55; %H, 4.99; %N, 29.77; Found: %C, 59.44; %H, 4.93; %N, 29.65.

EXAMPLE 6

α,α,5-Trimethyl-6H-imidazo[4,5-c]tetrazolo[1,5-a]quinoline-6-ethanol

Acetyl chloride (16 g, 0.020 mole) was added dropwise to a solution of [(4-amino-5-tetrazolo[1,5-c]quinolinyl)amino]-2-methyl-2-propanol (5 g, 0.18 mole, Example 4) in acetonitrile. The reaction mixture was stirred at ambient temperature for 4 hours. The resulting precipitate was isolated by filtration then dissolved in acetic acid (about 50 mL). This solution was refluxed for 2 hours then neutralized with carbonate. The crude product was isolated by filtration then recrystallized initially from hexane/ethyl acetate then from ethanol/ethyl acetate to provide α,α,5-trimethyl-6H-imidazo[4,5-c]tetrazolo[1,5-a]quinoline-6-ethanol as a solid, m.p. 202–205° C. Analysis: Calculated for $C_{15}H_{16}N_6O$: %C, 60.8; %H, 5.44; %N, 28.36; Found: %C, 60.68; %H, 5.48; %N, 28.28.

EXAMPLE 7

4-Hydrazino-1-(2-methylpropyl)-1H-imidazo[4,5-c]quinoline

4-Chloro-1-(2-methylpropyl)-1H-imidazo[4,5-c]quinoline (10.0 g, 0.0385 moles, U.S. Pat. No. 4,689,338 Example 77) was added to hydrazine (30 ml). The mixture heated rapidly to reflux. The solid dissolved with a vigorous heat of reaction then a precipitate formed as the reaction mixture refluxed. The reaction mixture was diluted with water. The precipitate was isolated by filtration then suspended in water (100 mL). The solid was brought into solution by the addition of acetic acid. The solution was filtered to remove traces of undissolved solid. The filtrate was made basic by the addition of ammonium hydroxide. The resulting precipitate was isolated by filtration, washed with water then dried to provide 8.0 g of crude product as a white solid. A sample of this material was recrystallized from methanol to provide 4-hydrazino-1-(2-methylpropyl)-1H-imidazo[4,5-c]quinoline, m.p. 202–205° C. Analysis: Calculated for $C_{14}H_{17}N_5$: %C, 65.86; %H, 6.71; %N, 27.43; Found: %C, 65.20; %H, 6.6; %N, 27.5.

EXAMPLE 8

6-(2-Methylpropyl)-6H-imidazo[4,5-c]tetrazolo[1,5-a]quinoline

A solution of sodium nitrite (2.0 g, 3 mmole) in water (5 mL) was added to a solution of 4-hydrazino-1-(2-methylpropyl)-1H-imidazo[4,5-c]quinoline (4.0 g, 15.7 mmole, Example 7) in a mixture of acetic acid (5 mL) and water (50 mL). The reaction mixture was stirred at ambient temperature for 15 minutes. A precipitate was isolated by filtration, washed with water then air dried to provide 4.1 g of crude product. This material was recrystallized from dichloromethane/ethanol to provide 3.0 g of 6-(2-methylpropyl)-6H-imidazo[4,5-c]tetrazolo[1,5-a]quinoline as a cream colored crystalline solid, m.p. 208–212° C. Analysis: Calculated for $C_{14}H_{14}N_6$: %C, 63.14; %H, 5.30; %N, 31.56; Found: %C, 62.60; %H, 5.2; %N, 31.5.

EXAMPLE 9

α,α-Dimethyl-6H-imidazo[4,5-c]tetrazolo[1,5-a]quinoline-6-ethanol

A suspension of 4-chloro-α,α-dimethyl-1H-imidazo[4,5-c]quinoline-1-ethanol (1.0 g, 3.6 mmole, U.S. Pat. No. 4,689,338 Example 189 Part D) in hydrazine (3 mL, 6.9 mmole) was heated on a steam bath for 1 hour then diluted with water. The resulting precipitate was isolated by filtration. The solid was dissolved in a mixture of acetic acid (2 mL) and water (15 mL) then combined with a solution of sodium nitrite (0.5 g) in water. The resulting precipitate was isolated by filtration, washed with water and dried to provide 0.71 g of α,α-dimethyl-6H-imidazo[4,5-c]tetrazolo[1,5-a]quinoline-6-ethanol as a white solid, m.p. 246–247° C. (shrunk at 230° C.). Analysis: Calculated for $C_{14}H_{14}N_6O$: %C, 59.56; %H, 5.00; %N, 29.77; Found: %C, 59.45; %H, 5.06; %N, 29.51.

EXAMPLE 10

1(2-Methylpropyl)-N-triphenylphosphinyl-1H-imidazo[4,5-c]quinolin-4-amine 6-(2-Methylpropyl)-6H-imidazo[4,5-c]tetrazolo[1,5-a]quinoline (0.2 g, 0.75 mmole, Example 8), triphenylphosphine (0.4 g, 1.5 mmole) and 1,2-dichlorobenzene (5 mL) were combined and heated at reflux overnight. The reaction mixture was concentrated under vacuum then diluted with cyclohexane (25 mL). The resulting precipitate was isolated by filtration, washed with cyclohexane then dried to provide 1-(2-methylpropyl)-N-triphenylphosphinyl-1H-imidazo[4,5-c]quinolin-4-amine as a solid, m.p. 209–210° C. Analysis: Calculated for $C_{32}H_{29}N_4P$: %C, 76.78; %H, 5.84; %N, 11.19; Found: %C, 76.03; %H, 5.87; %N, 11.09.

EXAMPLE 11

4-Amino-α,α-dimethyl-1H-imidazo[4,5-c]quinoline-1-ethanol

Triphenylphosphine (4.5 g, 17.0 mmole) was added to a mixture of α,α-dimethyl-6H-imidazo[4,5-c]tetrazolo[1,5-a]quinoline-6-ethanol (2.4 g, 8.5 mmole, Example 9) and 1,2-dichlorobenzene. The reaction mixture was heated at reflux for 3 hrs then concentrated under vacuum. The residue was combined with methanol (400 mL) and hydrochloric acid (50 mL of 0.5N) then heated on a steam bath for 2 hours. The resulting precipitate was isolated by filtration then washed with ether. The solid was dissolved in water and the solution was made basic with 10% sodium hydroxide. After stirring for 30 minutes, the reaction mixture was filtered. The collected solid was rinsed with water and ether then recrystallized from N,N-dimethylformamide/ethanol to provide about 1 g of 4-amino-α,α-dimethyl-1H-imidazo[4,5-c]quinoline-1-ethanol as a solid, m.p, 271–273° C. Analysis: Calculated for $C_{14}H_{16}N_4O$: %C, 65.6; %H, 6.29; %N, 21.86; Found: %C, 65.37; %H, 6.26; %N, 21.61.

EXAMPLE 12

1-(2-Methylpropyl)-1H-imidazo[4,5-c]quinolin-4-amine 1-(2-Methylpropyl)-N-triphenylphosphinyl-1H-imidazo[4,5-c]quinolin-4-amine (100 mg, Example 10) was suspended in a mixture of methanol (3 mL) and hydrochloric acid (10 mL of 0.5N). The mixture was heated on a steam bath for 2 hours then allowed to stand at ambient temperature overnight. The reaction mixture was filtered. The filtrate was made basic with 10% sodium hydroxide. The resulting precipitate was isolated by filtration then dried to provide 1-(2-methylpropyl)-1H-imidazo[4,5-c]quinolin-4-amine. The spectral properties of this material matched those of an authentic sample.

EXAMPLE 13

4-Nitrotetrazolo[1,5-a]quinolin-5-ol

Aqueous sodium hydroxide (30 g of 50%) was added to a suspension of 2-methyl-[(4-nitro-5-tetrazolo[1,5-a]quinolinyl)amino]-2-propanol (34.0 g, 0.1125 mole, Example 3) in water (500 mL). The mixture was heated on a steam bath and the solid dissolved rapidly. The solution was heated for about 30 minutes and then upon stirring a solid began to precipitate. The mixture was made acidic with 6N hydrochloric acid. The resulting solid was isolated by filtration; washed in succession with water, ethanol and ether; then dried under vacuum at 100° C. to provide 23.2 g of crude product as a pale yellow/green solid. A sample (3.2 g) was recrystallized initially from methanol/dichloromethane and then from toluene to provide 4-nitrotetrazolo[1,5-a]quinolin-5-ol. Analysis: Calculated for $C_9H_5N_5O_3$: %C, 46.76; %H, 2.18; %N, 30.29; Found: %C, 46.85; %H, 2.23; %N, 29.91.

EXAMPLE 14

4-Nitrotetrazolo[1,5-a]quinolin-5-yl] trifluoromethanesulfonate

Triethylamine (0.6 mL, 4.32 mmole) was added to a suspension of 4-nitrotetrazolo[1,5-a]quinolin-5-ol (1.0 g, 4.32 mmoles, Example 2) in dichloromethane (20 mL). The reaction mixture was cooled to 0° C. Triflic anhydride (0.73 mL, 4.32 mmole) was added. The reaction mixture was stirred for 3 hours at 0° C. The reaction mixture was diluted with dichloromethane (50 mL), washed with 0.5 N hydrochloric acid, dried over magnesium sulfate and concentrated under vacuum. The residue was combined with hexanes (100 mL), refluxed for 15 minutes and filtered. A solid precipitated from the filtrate on cooling. The solid was isolated by filtration and dried to provide 0.2 g of 4-nitrotetrazolo[1,5-a]quinolin-5-yl] trifluoromethanesulfonate as a white solid, m.p. 132–134° C. Analysis: Calculated for $C_{10}H_{14}F_3N_5O_5S$: %C, 33.07; %H, 1.11; %N, 19.28; Found: %C, 33.19; %H, 1.28; %N, 19.61.

EXAMPLE 15

N-(2-Methylpropyl)-4-nitrotetrazolo[1,5-a]quinolin-5-amine

Isobutylamine (1 mL) was added to a solution of 4-nitrotetrazolo[1,5-a]quinolin-5-yl] trifluoromethanesulfonate (0.5 g, 1.37 mmole, Example 14) in dichloromethane (50 mL), The reaction mixture was stirred at ambient temperature for 4 hours, diluted with dichloromethane (50 mL), washed with water (2×50 mL), dried over magnesium sulfate then concentrated under vacuum. The residue was purified by filtering through a layer of silica gel eluting with 2% methanol in dichloromethane. The resulting yellow solid was recrystallized from ethyl acetate to provide 0.31 g of N-(2-methylpropyl)-4-nitrotetrazolo[1,5-a]quinolin-5-amine, m.p. 152–154° C. Analysis: Calculated for $C_{13}H_{14}N_6O_2$: %C, 54.54; %H, 4.93; %N, 29.35; Found: %C, 54.45; %H, 4.73; %N, 29.47.

EXAMPLE 16

$N^5$-(2-Methylpropyl)tetrazolo[1,5-a]quinoline-4,5-diamine

N-(2-Methylpropyl)-4-nitrotetrazolo[1,5-a]quinolin-5-amine (1.0 g, 3.5 mmole, Example 15), ethanol (100 mL) and Pt/C were placed in a Paar apparatus. The mixture was hydrogenated at 50 psi ($3.44 \times 10^5$ Pa). The reaction mixture was filtered to remove the catalyst then concentrated under vacuum. The residue was recrystallized from ethyl acetate to provide 0.35 g of $N^5$-(2-methylpropyl)tetrazolo[1,5-a]quinoline-4,5-diamine as off white needles, m.p. 148–150° C. Analysis: Calculated for $C_{13}H_{16}N_6$: %C, 60.92; %H, 6.29; %N, 32.79; Found: %C, 60.94; %H, 6.25; %N, 32.93.

EXAMPLE 17

6-(2-Methylpropyl)-6H-imidazo[4,5-c]tetrazolo[1,5-a]quinoline $N^5$-(2-Methylpropyl)tetrazolo[1,5-a]quinoline-4,5-diamine (0.2 g, 0.78 mmole, Example 16) was combined with diethoxymethyl acetate (2 mL) and heated on a steam bath for 3 hours. Water (10 mL) and 10% sodium hydroxide (2 mL) were added and the reaction mixture was heated on a steam bath for 1 hour. A solid was isolated by filtration then recrystallized from methanol/ethyl acetate to provide 0.16 g of 6-(2-methylpropyl)-6H-imidazo[4,5-c]tetrazolo[1,5-a]quinoline as a white crystalline solid, m.p. 210–212° C. Analysis: Calculated for $C_{14}H_{14}N_6$: %C, 63.14; %H, 5.30; %N, 31.56; Found: %C, 63.12; %H, 5.32; %N, 31.61.

EXAMPLE 18

N-(1,1-Dimethylethyl)-4-nitrotetrazolo[1,5-a]quinolin-5-amine

Triethylamine (6 mL), 4-nitrotetrazolo[1,5-a]quinolin-5-ol (8.7 g, 37.6 mmole, Example 13) and dichloromethane (100 mL) were combined and stirred at ambient temperature until a solution was obtained. The solution was cooled to −15° C. Triflic anhydride (6.5 mL) was added in portions to the cooled solution. The reaction mixture was allowed to warm to ambient temperature then filtered through a layer of silica gel. The filtrate was washed with cold dilute hydrochloric acid then dried over magnesium sulfate. Triethylamine (5.25 mL) was added to the dichloromethane solution and the resulting mixture was stirred for about 10 minutes. tert-Butylamine (4.2 mL) was added dropwise to the reaction mixture. The reaction mixture was heated on a steam bath for about 15 minutes. The resulting solid was isolated by filtration then purified by silica gel chromatography to provide the crude product as a yellow solid. This material was recrystallized from ethanol/water to provide 5 g of N-(1,1-dimethylethyl)-4-nitrotetrazolo[1,5-a]quinolin-5-amine. The structure was confirmed by nuclear magnetic resonance spectroscopy.

EXAMPLE 19

$N^5$-(1,1-Dimethylethyl)tetrazolo[1,5-a]quinoline-4,5-diamine

N-(1,1-dimethylethyl)-4-nitrotetrazolo[1,5-a]quinolin-5-amine (4.2 g, Example 18), ethanol (100 mL) and Pt/C (0.5 g) were placed in a Paar apparatus. The mixture was hydrogenated. The reaction mixture was filtered to remove catalyst then concentrated to dryness under vacuum. The residue was recrystallized from ethyl acetate/dichloromethane to provide $N^5$-(1,1-dimethylethyl)tetrazolo[1,5-a]quinoline-4,5-diamine as a pale blue crystalline solid.

EXAMPLE 20

6-(1,1-Dimethylethyl)-6H-imidazo[4,5-c]tetrazolo[1,5-a]quinoline

Diethoxymethyl acetate (1.9 mL) was added dropwise to a solution of $N^5$-(1,1-dimethylethyl)tetrazolo[1,5-a]quinoline-4,5-diamine (1.5 g, 5.9 mmole, Example 19) in acetic acid (15 mL). The reaction mixture was heated on a steam bath for 1 hour then made basic with sodium hydroxide. The resulting precipitate was isolated by filtration then recrystallized from ethanol to provide 6-(1,1-dimethylethyl)-6H-imidazo[4,5-c]tetrazolo[1,5-a]quinoline, m.p. 224–226° C. Analysis: Calculated for $C_{14}H_{14}N_6$: %C, 63.13; %H, 5.29; %N, 31.56; Found: %C, 62.90; %H, 5.44; %N, 31.52.

EXAMPLE 21

6H-Imidazo[4,5-c]tetrazolo[1,5-a]quinoline 6-(1,1-Dimethylethyl)-6H-imidazo[4,5-c]tetrazolo[1,5-a]quinoline (1 g, 3.8 mmole, Example 20) was added to hydrochloric acid (5 mL of 6N); water (20 mL) was added and the mixture was heated on a steam bath for 1 hour. The reaction mixture was allowed to cool to ambient temperature then made basic (pH 11) by the addition of sodium hydroxide solution. The resulting precipitate was isolated by filtration, dried then recrystallized from N,N-dimethylformamide to provide 0.65 g of the desired product as a solid. A sample of this material was refluxed in a large amount of dichloromethane/methanol, isolated by filtration, then dried to provide 6H-imidazo[4,5-c]tetrazolo[1,5-a]quinoline as a solid, m.p. >300° C. Analysis: Calculated for $C_{10}H_6N_6$: %C, 57.14; %H, 2.88; %N, 39.98; Found: %C, 56.89; %H, 3.10; %N 39.34. The structure was confirmed by both mass spectroscopy and nuclear magnetic resonance spectroscopy.

What is claimed is:

1. A compound of Formula VII

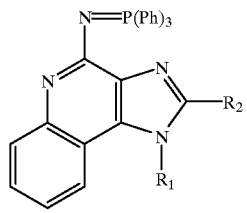

VII wherein $R_1$ is selected from the group consisting of hydrogen, alkyl of one to about six carbon atoms, hydroxy alkyl wherein the alkyl moiety contains one to about 6 carbon atoms, and arylalkyl wherein the alkyl moiety contains one to about three carbon atoms; and $R_2$ is selected from the group consisting of hydrogen, alkyl of one to about four carbon atoms, alkoxyalkyl wherein the alkoxy moiety contains one to about four carbon atoms and the alkyl moiety contains one to about four carbon atoms, hydroxyl alkyl wherein the alkyl moiety contains one to about four carbon atoms, haloalkyl wherein the alkyl moiety contains one to about four carbon atoms, and aryloxymethyl.

2. A compound according to claim 1 wherein $R_1$ is selected from the group consisting of hydrogen, 2-methylpropyl, 2-hydroxy-2-methylpropyl, benzyl and phenylethyl and $R_2$ is selected from the group consisting of hydrogen, methyl, ethoxymethyl, and benzyl.

3. A compound according to claim 2 wherein $R_1$ is 2-methylpropyl and $R_2$ is hydrogen.

4. A compound of Formula XI

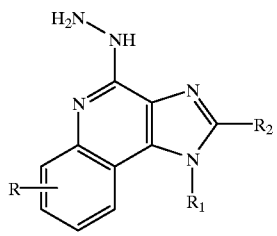

XI wherein $R_1$ is selected from the group consisting of hydrogen, alkyl of one to about six carbon atoms, hydroxy alkyl wherein the alkyl moiety contains one to about 6 carbon atoms, and arylalkyl wherein the alkyl moiety contains one to about three carbon atoms; and $R_2$ is selected from the group consisting of hydrogen, alkyl of one to about four carbon atoms, alkoxyalkyl wherein the alkoxy moiety contains one to about four carbon atoms and the alkyl moiety contains one to about four carbon atoms, hydroxyl alkyl wherein the alkyl moiety contains one to about four carbon atoms, haloalkyl wherein the alkyl moiety contains one to about four carbon atoms, and aryloxymethyl.

5. A compound according to claim 4 wherein $R_1$ is selected from the group consisting of hydrogen, 2-methylpropyl, 2-hydroxy-2-methylpropyl, benzyl and phenylethyl and $R_2$ is selected from the group consisting of hydrogen, methyl, ethoxymethyl, and benzyl.

6. A compound according to claim 5 wherein $R_1$ is 2-methylpropyl and $R_2$ is hydrogen.

* * * * *